United States Patent [19]

Yost et al.

[11] Patent Number: 5,448,995
[45] Date of Patent: Sep. 12, 1995

[54] METHOD AND APPARATUS FOR NON-INVASIVE EVALUATION OF DIAPHRAGMATIC FUNCTION

[75] Inventors: William T. Yost, Newport News, Va.; Juliette L. Wait, Dallas, Tex.; Patricia A. Nahormek, Newport News, Va.; John H. Cantrell, Tabb, Va.; Pamela D. Hanna-Hawver, Blackburg, Va.

[73] Assignee: The United States of America as represented by the Administrator of the National Aeronautics and Space Administration, Washington, D.C.

[21] Appl. No.: 195,500

[22] Filed: Feb. 14, 1994

[51] Int. Cl.⁶ .............................................. A61B 8/00
[52] U.S. Cl. .............................................. 128/660.07
[58] Field of Search ............... 128/660.06, 660.07, 128/661.02, 661.03; 364/413.02, 413.03, 413.04

[56] References Cited

U.S. PATENT DOCUMENTS

| | | | |
|---|---|---|---|
| 4,359,056 | 11/1982 | Carlson | 128/660 |
| 4,520,830 | 6/1985 | Flanagan, III | 128/660 |
| 4,574,635 | 3/1986 | 't Hoen | 128/660 |
| 4,575,799 | 3/1986 | Miwa et al. | 364/414 |
| 5,031,627 | 7/1991 | Yost et al. | 128/660.06 |
| 5,299,576 | 4/1994 | Shiba | 128/660.07 |

OTHER PUBLICATIONS

*Effect of pressure and timing of contraction on human diaphragm fatigue.* F. Bellemare and A. Grassino, J. Appl. Physiol.: Respirat. Environ. Exercise Physiol. 53(5): 1190–1195, 1982.

*Diaphragmatic thickness–lung volume relationship in vivo.* Juliette L. Wait, Patricia A. Nahormek, William T. Yost, and Dudley F. Rochester, J. Appl. Physiol. 67(4): 1560–1568, 1989.

Primary Examiner—George Manuel
Attorney, Agent, or Firm—Kimberly A. Chasteen

[57] ABSTRACT

A method for non-invasive evaluation of diaphragmatic function in humans measures the thickness of the diaphragm in real time with an ultrasonic device, and displays the variations of diaphragm thickness versus time. Formulae are given for calculating a quantitative value for the reserve fatigue capacity of a patient's diaphragm from data obtained by measuring the time limits for maintaining a constant breathing pattern on the display at two different pressure differentials in series with the patient's airways. An apparatus for displaying the diaphragm thickness in real time is also described. The method can be used both on healthy patients and on patients with so severe breathing dysfunctions that they require breathing support from respirators.

6 Claims, 2 Drawing Sheets

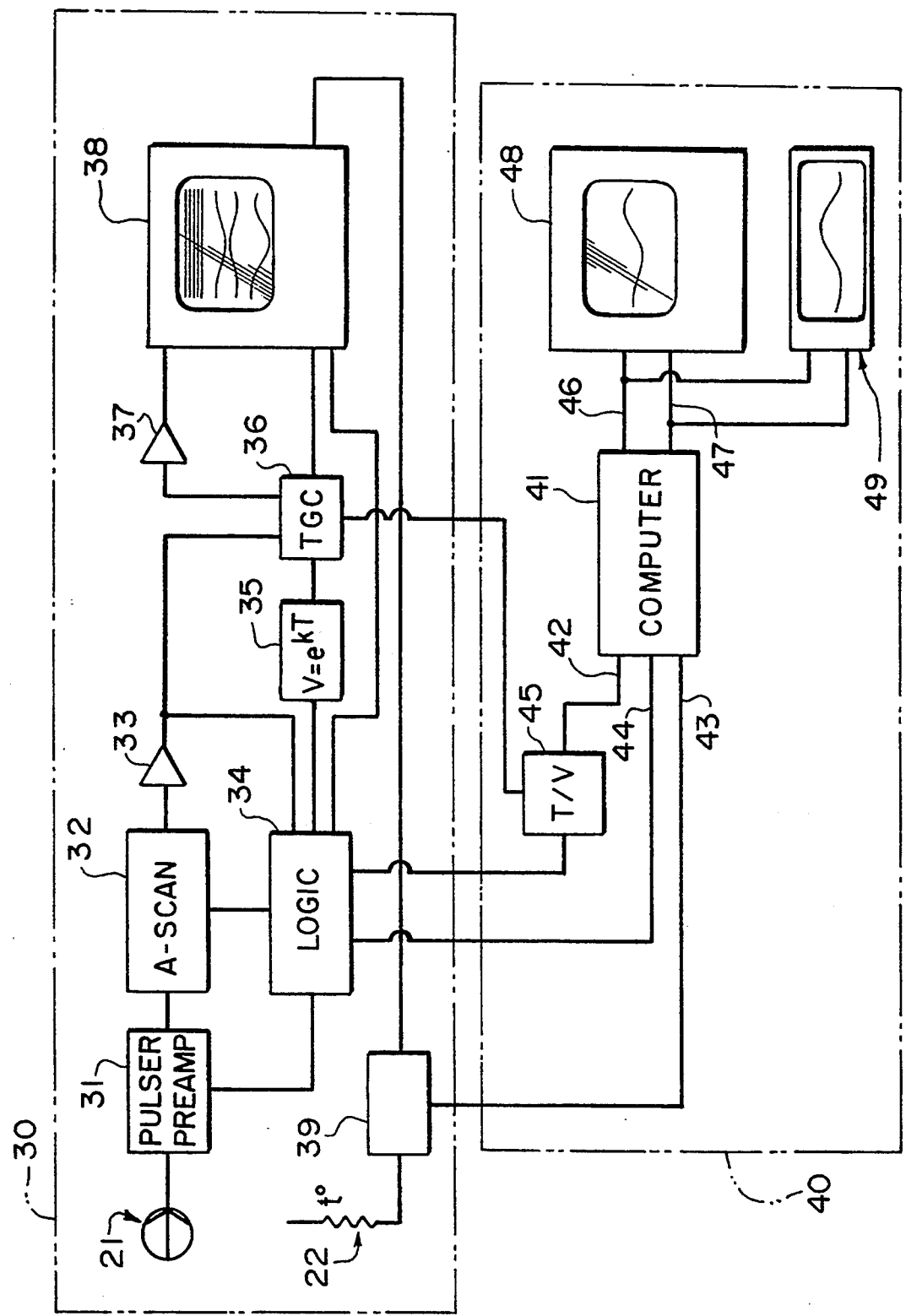

METHOD AND APPARATUS FOR NON-INVASIVE EVALUATION OF DIAPHRAGMATIC FUNCTION

ORIGIN OF THE INVENTION

The invention described herein was made in the performance of work done by employees of the U.S. Government and may be manufactured and used by or for the government for governmental purposes without the payment of any royalties thereon or therefore.

BACKGROUND OF THE INVENTION

1. Field of the Invention

The invention relates in general to evaluation of breathing problems, and specifically to a non-invasive method and apparatus for evaluating diaphragm function and diaphragm fatigue in patients suffering from emphysema and other pulmonary related dysfunctions.

2. Description of the Related Art

Oxygen enters the human body from air pumped into the lungs during breathing. The lungs expand and contract passively with the volume of a lung cavity formed by a rib cage and a muscle called a diaphragm. When the diaphragm contracts, the volume of the lung cavity increases and the lungs fill with air ("inspiration"). Expansion of the rib cage has the same effect, and normal inspiration involves both contraction of the diaphragm and expansion of the rib cage. The total volume of air inspired during a full inspiration cycle is called "the tidal volume." The relative part of the tidal volume contributed by the contraction of the diaphragm and by the expansion of the rib cage varies between individuals, and may vary with time in the same individual, but contraction of the diaphragm is necessary for effective inspiration.

Expiration starts when the diaphragm relaxes and the rib cage contracts, and ends when the lung cavity has reached minimum volume. The diaphragm can not actively aid in the expiration, it is simply pressed up against the lung cavity by the prevailing pressure in the abdomen when it relaxes. The rib cage also contracts passively when the expansion muscles in the rib cage relax. Extra expiration effort can, however, be contributed by contraction muscles in the rib cage and in the abdomen.

A healthy person feels no strain or fatigue in normal breathing. In order to induce breathing fatigue in a healthy person, the person must be forced to breath through a restricted mouthpiece, which adds a substantial pressure drop in series with the airways.

Known methods for evaluation of diaphragm function in human patients require time-intensive set-ups, and require measurement of the pressure differential across the diaphragm by means of two pressure sensors, which must be swallowed by the patient. The two pressure sensors must be arranged to measure the trans-diaphragmatic pressure and the gastric pressure. The actual evaluation requires time consuming and strenuous breathing exercises by the patient through restricted mouthpieces, while air flow and the pressure differential are measured. A comprehensive description of the known procedure for evaluating diaphragmatic fatigue in healthy persons is given in a publication by F. Bellemare and A. Grassino, "Effect of pressure and timing of contraction on human diaphragm fatigue." *Journal of Applied Physiology: Resp. Environ. Exercise Physiol.* 53(5): 1190–1195, 1982.

Patients with emphysema have obstructed lungs and airways. The obstructions resist airflow, and cause a pressure drop that must be overcome by the breathing mechanism. In severe cases of emphysema, normal breathing at rest can lead to diaphragmatic fatigue. At that stage, the patient requires breathing assistance. First, he will be given oxygen, which increases the rate of oxygen transfer in the lungs and thereby lowers the tidal volume required per breath, so shallower and less fatigue breathing will satisfy the patient's oxygen need. If this is not sufficient, the patient must be connected to a respirator for assisted breathing.

A respirator provides a constant positive breathing pressure during inspiration, maintaining a suitable inspiration period and a tidal volume that will provide proper oxygenation. During expiration, the respirator maintains an opposite pressure differential, providing a suitable expiration period. The respirator thus compensates for the pressure drops in the obstructed airways. Depending on the amount of pressure provided by the respirator, the work to be performed by the diaphragm and the rib cage in each breathing cycle can either be reduced to a tolerable level, or entirely eliminated. A respirator, however, must be set to provide a sufficient tidal volume, and it is not possible to determine from the pressure in the respirator if the patient takes any active part in the breathing. This is unfortunate, because the muscle tone of the diaphragm will deteriorate with time when breathing is provided passively by a respirator. If the patient remains on the respirator too long, he may eventually lose his ability to breath effectively on his own.

Breathing dysfunction can also be caused by paralysis of the diaphragm and/or the rib cage muscles, for instance after trauma to the brain or to the spinal cord. In such cases, the patient must also be connected to a respirator to survive. Even in such cases it would be helpful to establish if, or when, the patient regains partial or full ability to breathe on his own, without first disconnecting the respirator entirely.

Known methods for evaluating diaphragmatic function by measurement of the pressure differential across the diaphragm by means of pressure transducers swallowed by the patient are not feasible for patients on a respirator. Doctors must accordingly rely on experience to guess when, or if, the respirator could be removed. Even temporary removal of a respirator may cause severe discomfort to the patient, and the doctor would still not be able to determine what degree of breathing ability the patient had achieved.

A publication by J. Wait, P. Nahormek, W. Yost, and D. Rochester: "Diaphragmatic thickness-lung volume relationship in vivo," *J. Appl. Physiol.* 67(4): 1560–1568, 1989, describes a non-invasive method for measuring the thickness of a human diaphragm based on M-mode ultrasonography, and finds a linear relationship between changes in the diaphragm thickness and the volume of air inspired into the lung. The publication does not discuss evaluation of diaphragmatic function or fatigue.

SUMMARY OF THE INVENTION

Accordingly, it is an object of the invention to provide a method for evaluation of diaphragmatic function in patients with severe breathing dysfunctions.

It is a further object of the invention to provide a method for evaluation of diaphragmatic function in patients requiring assisted breathing by mechanical respirators.

It is still a further object of the invention to provide apparatus for non-invasive evaluation of diaphragmatic function in patients using ultrasound.

In order to achieve the foregoing and other objects, in accordance with the purposes of the present invention as described therein, a method for non-invasive evaluation of diaphragmatic function comprises the steps of providing real time ultrasonic measuring of the thickness of a diaphragm in a patient, and displaying the diaphragm thickness as a function of time.

An apparatus for non-invasive evaluation of diaphragmatic function comprises means for real time ultrasonic measurement of the thickness of a diaphragm in a patient and means for displaying the diaphragm thickness as a function of time. As embodied herein, there is an ultrasonic transducer arranged on the lower rib cage of a patient between ribs to transmit ultrasonic pulses through the lateral part of the patients diaphragm and to receive pulse echoes from the interior of the rib cage, means for receiving and amplifying ultrasonic signals received by the transducer, means for selecting a pair of signals emanating respectively from the parietal pleura side and the peritoneum side of the diaphragm as a result of one transmitted ultrasonic pulse, means for determining the time differential between the pair of signals, means for repeating the pulse transmissions at constant time intervals, and means for displaying the time differential between the pair of signals from subsequent pulse transmissions versus time.

BRIEF DESCRIPTION OF THE DRAWINGS

The present invention and the objects achieved by it will be understood from the description herein, with reference to the accompanying drawings, in which:

FIG. 4 is a block diagram of an apparatus according to the invention.

DETAILED DESCRIPTION OF A PREFERRED EMBODIMENT

Figure 1:
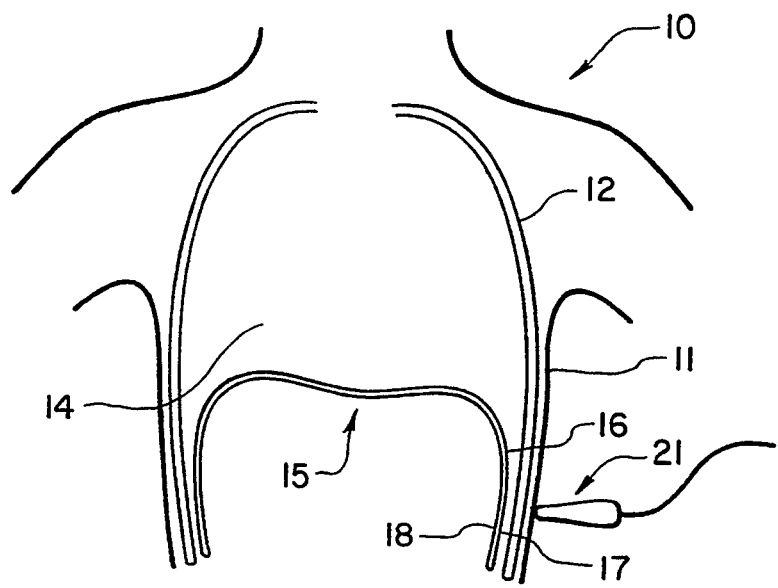
FIG. 1 is a simplified vertical section through a human chest and diaphragm, showing the placement of an ultrasonic transducer according to the present invention.

FIG. 1 is a vertical section of the chest of a human 10, shown in simplified form. A lung cavity 14 is enclosed within a rib cage 12 with a dome shaped muscle called the diaphragm 15 closing the bottom of the rib cage 12. The lungs and related membranes fill the lung cavity 14, but they are not shown in FIG. 1 for the sake of simplicity. The lung volume changes passively with changes in the volume of the lung cavity 14 caused by expansion and contraction of the diaphragm 15 and of muscles in the rib cage 12.

Diaphragm 15 has side wall 16 having inner and outer side surfaces 18 and 17. An ultrasonic transducer 21 located at the side of the lower part of the rib cage 12 is aimed towards the centerline of the rib cage 12. The transducer 21 has a tip diameter of about ⅛ inch, so when it is pressed against skin 11 of the patient it fits in a space between two ribs. The transducer 21 is connected to a conventional M-mode ultrasonic device 30 (FIG. 4), which provides a conventional sonogram. The ultrasonic device 30 will be described below with reference to FIG. 4.

Figure 2:
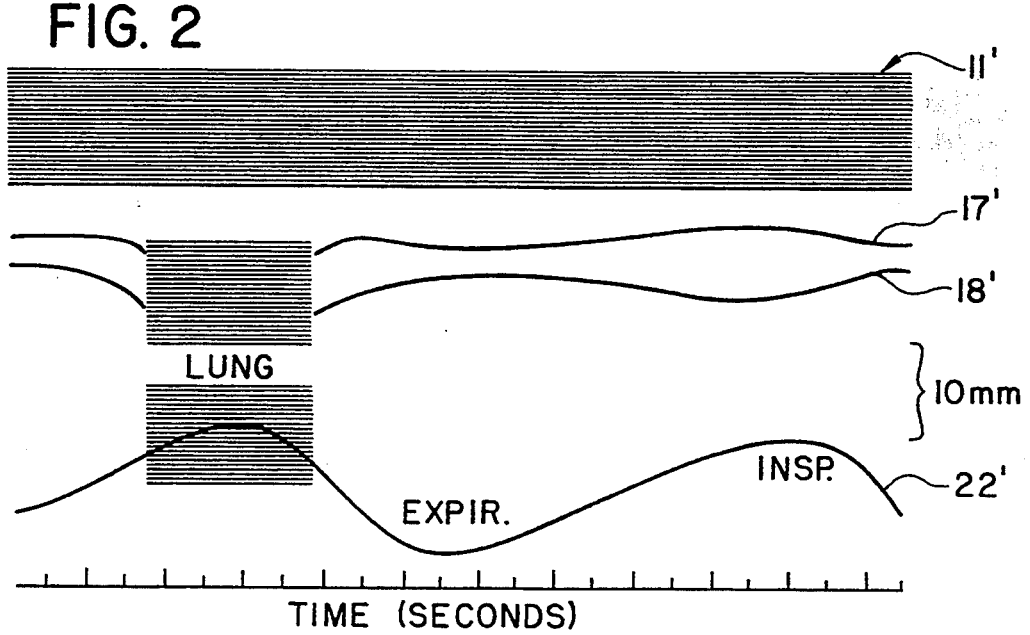
FIG. 2 is a sonogram obtained by the transducer in FIG. 1, showing diaphragm motion during breathing.

FIG. 2 is a retouched picture of a sonogram obtained when the patient 10 first makes a very deep breath, so the top of the diaphragm 15 moves below the transducer 21, and thereafter breathes normally. Lines 11' and 12' represent the skin surface 11 and the inside of the rib cage 12. When the diaphragm 15 is below the transducer 21, the rest of the display represents the air filled lungs, but when a side wall 16 of the diaphragm 15 enters the path of the ultrasonic wavefront, both side surfaces 17 and 18 of the wall 16 become visible as lines 17' and 18' in the sonogram. The lower graph in FIG. 2 is a signal 22' obtained from a thermistor 22 (FIG. 4) sensing the temperature of the air flow in the airways of the patient 10. The thermistor display is used to distinguish between the inspiration part and the expiration part of the breathing cycle, as is common in breathing analysis.

The distance between lines 17' and 18' in the sonogram represents the thickness of the diaphragm wall 16. The publication by J. Wait et al. referenced above proves that the thickness of the diaphragm wall 16 displayed in a sonogram is a very accurate representation of the real thickness of the diaphragm wall 16.

FIG. 2 clearly shows that the thickness of the diaphragm wall 16 varies with time, increasing during inspiration and decreasing during expiration. This is consistent with the function of all skeletal muscles, which increase in cross section when they contract.

Figure 3:
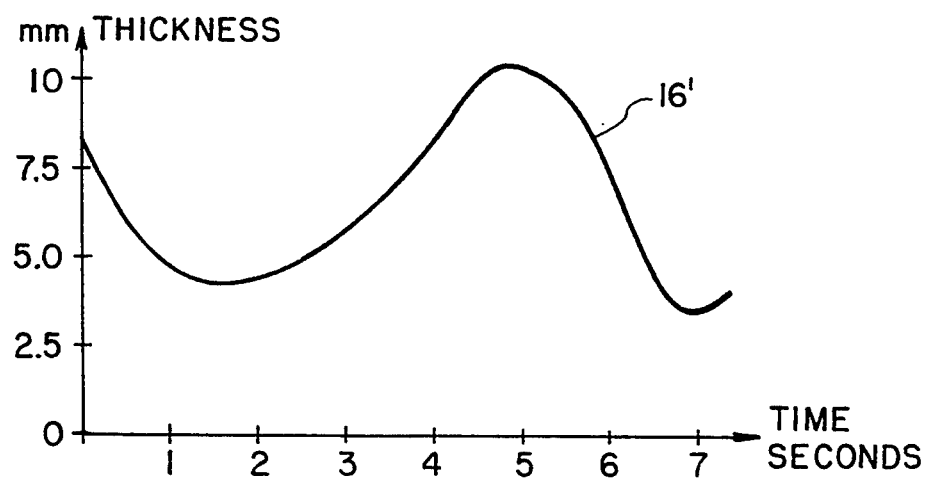
FIG. 3 is a diagram showing diaphragm thickness versus time corresponding to the sonogram of FIG. 2.

According to the invention, the diaphragmatic function of a patient on a mechanical respirator can be evaluated without any discomfort to the patient by observing the thickness of the diaphragm wall 16 as a function of time as measured by ultrasonic methods. Such a graph showing the thickness variations in a diaphragm wall 16 with time is shown in FIG. 3. The graph of FIG. 3 corresponds to the right hand part of the sonogram of FIG. 2, but the thickness variations shown by line 16' are much easier to see in FIG. 3. Apparatus for performing a conversion of sonogram readings to thickness display will be described later with reference to FIG. 4.

A doctor viewing a display of diaphragm thickness as a function of time will immediately see if the patient is actively breathing, because only active breathing will produce a variation in thickness with time. The thickening of a muscle, such as the diaphragm wall 16, is a function of active muscle contraction only. Passive deflection of the diaphragm 15 induced by a mechanical respirator will not cause any thickening of the diaphragm wall 16, but will only cause the slack diaphragm 15 to buckle during inspiration and to unfold again during expiration.

If passive or near passive breathing is observed, the doctor will ask the patient to try to breath actively in synchronism with the respirator. The thickness display will immediately show if the patient is able to do so, and the display can be made visible to the patient, so he gets immediate feedback on his efforts. The pressure differential provided by the respirator can then be lowered while the patient maintains a constant pattern in the thickness display. The amount of change in respirator pressure that makes the patient unable to maintain a steady breathing pattern can be used as a qualitative gauge of progress in the patient's diaphragmatic function if the pressure change is compared from day to day.

The invention also makes a quantitative determination of both the maximum trans-diaphragmatic pressure that the patient can voluntarily develop under isostatic conditions and the possible reserve fatigue capacity of the diaphragm, without need for direct measurement of trans-diaphragmatic pressure.

The publication by F. Bellemare and A. Grassino referenced above defines a quantity representing the time integral of diaphragmatic tension per breath, which they call "TTdi." The term Time Tension Index ("TTI") is used herein for this quantity as follows:

$$(Pdi/Pdimax)(T_1/T_{tot}) \qquad (1)$$

where:
Pdi is the average trans-diaphragmatic pressure during inspiration.
Pdimax is the maximum trans-diaphragmatic pressure the person can develop under isometric conditions.
$T_1$ is the inspiration time.
$T_{tot}$ is the total time for a breathing cycle.

Bellemare and Grassino found that diaphragmatic fatigue will not occur if TTI is less than 0.15. They also developed a useful formula for the correlation between TTI and the time limit in minutes ($T_{LIM}$) for a patient's ability to maintain breathing cycles with a fixed diaphragmatic tension:

$$T_{LIM}=0.1(TTI)^{-3.6} \qquad (2a)$$

or:

$$TTI=(T_{LIM}/0.1)^{-1/3.6} \qquad (2b)$$

The Time Tension Index has an quiescent ("resting") value $TTI_o$ in the absence of any pressure differential $\Delta P$ in series with the airways. The reserve fatigue capacity of the diaphragm is, according to Bellemare and Grassino, the difference between 0.15 and $TTI_o$. This quiescent value $TTI_o$ for the Time Tension Index can not be determined through measurement of $T_{LIM}$, because there is no limit to the duration of breathing at rest, neither in a healthy person, nor in a person on a respirator at full respirator pressure.

Assume, however, that the respirator pressure is reduced to a first value $\Delta P_1$ that enables the patient to maintain a constant breathing pattern only for a limited time $T_{LIM1}$, while the breathing pattern is monitored on a display of diaphragm thickness versus time according to the invention. The value for $T_{LIM1}$ in minutes is measured and inserted in equation (2b), which yields a corresponding first value $TTI_1$ for the Time Tension Index for the breathing test at pressure differential $\Delta P_1$. Assume next that, after a rest period, the respirator pressure is reduced to a second value $\Delta P_2$ that also enables the patient to maintain a constant breathing pattern only for a limited time $T_{LIM2}$, while the breathing pattern is maintained as in the first case, as monitored on the display of diaphragm thickness versus time according to the invention. The second value for $T_{LIM2}$ in minutes is also measured and inserted in equation (2b), which yields a corresponding second value $TTI_2$ for the Time Tension Index for the breathing test at the second pressure differential $\Delta P_2$.

The average trans-diaphragmatic pressure Pdi during each of the two breathing tests described above consists of two additive pressure components:

$$Pdi_1=Pdi_o+\Delta P_1 \qquad (3a)$$

$$Pdi_2=Pdi_o+\Delta P_2 \qquad (3b)$$

where:

$Pdi_1$ and $Pdi_2$ are the actual, but unknown, trans-diaphragmatic pressures during the two different breathing tests.
$Pdi_o$ is the quiescent trans-diaphragmatic pressure for the patient.
$\Delta P_1$ and $\Delta P_2$ are the two known pressure differentials in series with the airways during the two breathing tests.

Note that $\Delta P_1$ and $\Delta P_2$ must be entered as negative values when a respirator aids in breathing, but as positive values when the pressure differentials are caused by restrictions inserted in series with the airways of healthy people to induce sufficient fatigue to make measurements of $T_{LIM}$ possible.

By replacing Pdi in equation (1) by $Pdi_1$ and $Pdi_2$, and also replacing $(Pdi_o/Pdimax)(T_1/T_{tot})$ by $TTI_o$, we get the following two equations:

$$TTI_1=TTI_o+(\Delta P_1/Pdimax)(T_1/T_{tot}) \qquad (4a)$$

$$TTI_2=TTI_o+(\Delta P_2/Pdimax)(T_1/T_{tot}) \qquad (4b)$$

All the symbols have the same meaning as before. Note that $T_1/T_{tot}$ is the same in both cases, because the breathing pattern was kept constant. $T_1/T_{tot}$ will normally be about $\frac{1}{3}$.

When equation (4a) is subtracted from equation (4b) and rearranged, there is obtained:

$$Pdimax=(\Delta P_2-\Delta P_1)/(TTI_2-TTI_1)\cdot(T_1/T_{tot}) \qquad (5)$$

All the parameters to the right of the equal sign are known, so Pdimax can now be calculated.

When equations (4a) and (4b) are added and the result is rearranged, there is obtained:

$$TTI_o=\tfrac{1}{2}[TTI_1+TTI_2-(\Delta P_1+\Delta P_2)/Pdimax\cdot(T_1/T_{tot}) \qquad (5)$$

Here, Pdimax was calculated from equation (5), and all of the other parameters to the right of the equal sign are known, so the quiescent value $TTI_o$ for the Time Tension Index can now be calculated.

The reserve fatigue capacity for the patient is then:

$$\Delta TTI_{reserve}=0.15 - TTI_o \qquad (7)$$

This reserve fatigue capacity is positive for healthy people, but negative for patients who can not breathe without a mechanical respirator.

By using the method according to the invention, it is thus possible to obtain quantitative data for the reserve fatigue capacity of a patient without measurement of trans-diaphragmatic pressure differential. The need for inserting pressure sensors in the patient's body is thus eliminated by the invention.

If the patient is too weak to perform even the simple breathing tests described above, quantitative data can not be obtained, but the invention still makes it possible to get a qualitative evaluation of the patient's breathing ability by observing how the display of diaphragm thickness varies with time when the respirator pressure is varied.

An apparatus for non-invasive evaluation of diaphragmatic function according to the invention will now be described with reference to FIG. 4, which is a block diagram for such an apparatus.

A first large block 30 in FIG. 4 represents a conventional ultrasonic device, commonly used for medical purposes. An ultrasonic transducer 21 is connected to a pulser/preamplifier 31. The pulser in the pulser/preamplifier 31 sends a series of voltage spikes to the transducer 21. Each voltage spike makes the transducer 21 transmit a sharp wavefront. The preamplifier in the pulser/preamplifier 31 amplifies signals generated by the transducer 21 when part of each wavefront is reflected by discontinuities. The transducer 21 is a high frequency device with a mid-frequency of about 15 MHz in the frequency domain, which means that the wavefronts are very steep in the time domain, and assures high distance resolution.

The pulser/preamplifier 31 is controlled by a logic module 34. The signals returned from the transducer 21 via the preamplifier in the pulser/preamplifier 31 are processed by an A-scan module 32, which also receives a control signal from the logic module 34. The control signal opens a gate in the A-scan module for a few micro-seconds shortly after a voltage spike has been transmitted to the transducer 21, so only reflected signals are processed by the A-scan module 32. The pulses passing the A-scan module are first amplified by a buffer 33, and then processed further by a TGC module 36, from which the pulses are transmitted via another buffer 37 to a display unit 38.

The display unit 38 converts a set of pulses resulting from each wavefront transmitted by the transducer 21 to a vertical column of dots on the monitor in the display unit 38. The vertical distance between dots represents the time delay between dots, and thereby the distance between successive discontinuities in the medium where the wavefront travels. The ratio between time differential and distance is determined by the speed of the ultrasonic wave. Subsequent series of pulses are displayed in separate columns next to each other along a time axis, so a real-time sonogram as illustrated in FIG. 2 is generated.

The display unit 38 also receives signals from a thermistor probe 22 via a thermistor module 39, which converts temperature differences sensed by the thermistor probe 22 to voltage differences that can be processed and displayed by the display unit 38. The thermistor is arranged in a mouthpiece in series with the airways of a patient, so it will sense increasing temperatures during expiration, when it is exposed to hot air from the lungs, and decreasing temperatures during inspiration, when cold outside air enters the mouthpiece. The thermistor signal will accordingly appear on the sonogram as a wave-shaped curve 22'(see FIG. 2), which makes it possible to clearly distinguish periods of inspiration from periods of expiration.

The display unit 38 receives synchronization signals from the logic unit 34, which ensures that the sonogram picture remains jitter free on a monitor in the display unit 38. The display unit 38 may include a strip chart recorder instead of, or in addition to, a monitor as indicated in FIG.4.

The TGC module 36 receives a voltage increasing exponentially with time from a ramp module 35, which also is controlled by the logic module 34. The TGC module 36 provides a gain increasing in proportion to the exponentially increasing voltage from the ramp module, so pulses coming late from the buffer 33 are amplified more than early pulses. This ensures that all pulses exiting the TGC have substantially equal amplitudes, so the display unit 38 can resolve all pulses with equal resolution. A detailed description of the time gain control function is described in U.S. Pat. 5,031,627 to Yost et al.

Apart from the time gain control circuits 35, 36, which are relatively new in the art, the ultrasonic device 30 described above is conventional apparatus, well known to those skilled in the art.

The second large block 40 in FIG. 2 contains circuits for providing a display of diaphragm thickness versus time, as required by the invention. A basic element in this part of the apparatus is a digital computer 41. The computer 41 has a first input 42, which contains an A/D converter. This input 42 receives copies of the pulses from the TGC module in the ultrasonic device 30 via a time/voltage converter 45. A second input 43 in the computer 41, which also contains an A/D converter, receives a signal from the thermistor module 39 in the ultrasonic device 30. A third input 44 in the computer 41 receives control pulses from the logic unit 34 in the ultrasonic device 30. The computer 41 contains D/A converters with output terminals 46, 47, so it can convert the results of its calculations into signals for display on a monitor 48 or a strip chart recorder 49.

The task of the computer 41 is to convert the time delay between a certain pair of pulses 17', 18', namely those returned from the parietal pleura side 17 and the peritoneum side 18 of the diaphragm wall 16, into signals that can be displayed as diaphragm thickness versus time. The conversion from time to thickness involves a simple calculation. Any person with computer skills will be able to write suitable software code for this purpose. The real objective is to distinguish the desired pair of pulses 17', 18' from the multitude of pulses returned from the transducer 21.

One way to select the desired pulse pair 17', 18' is to use the logic module 34 to control a gate in the time voltage converter 45, as indicated in FIG. 4. The logic module 34 in this case sends a first signal to open a gate in the time/voltage converter 45 a fixed first time interval after the logic unit 34 fires the pulser in the pulser/preamplifier 32, and a second signal to close the gate a fixed second time interval after the first signal to open the gate was sent. The correct pulse pair 17', 18' will be selected when: (i) the first time interval is larger than the time for receiving a reflection 12' from the inside of the rib cage 12, but shorter than the time for receiving a reflection 17' from the outside 17 of the diaphragm wall 16; and (ii) the sum of the first and the second time intervals is larger than the latest time for a reflection 18' from the inside 18 of the contracted diaphragm wall 16, but shorter than the time interval between successive firings of the transducer 21. The second requirement is easily satisfied, but the thickness of the muscles in the rib cage 12 will vary from patient to patient, so the first time interval must be adjustable. A manual adjustment can readily be achieved in practice by using the sonogram displayed on the display unit 38 as a guide.

Another method for selecting the right pair of pulses relies on the capabilities of the computer to make decisions based on algorithms expressed in software. In this case, all pulses processed by the TGC module 36 will be forwarded to the computer input 42 via the time/voltage converter 45, so they appear at the computer input 42 as a series of pulses on a voltage ramp. A suitable algorithm can, for instance, specify: "Select the second pair of pulses in each pulse series that are separated by a voltage difference larger than $\Delta V$." This algorithm will ensure that the clutter of closely spaced pulses generated by the rib cage 12 will be eliminated, because the voltage difference between these pulse pairs are too small (see FIG. 2). The next pair of pulses 12', 17', representing the inside of the rib cage 12 and the outside 17 of the diaphragm wall 16, will have a sufficient voltage difference, but they will be eliminated because they are not the second pair of such pulses. The next pair of pulses 17', 18', which is the desired pair, meets all the requirements in the algorithm, so it will be selected for conversion to thickness display. Any computer programmer can write software code to perform the specified algorithm. A detailed description of the software code for selecting the desired pair of pulses 17', 18' is accordingly not required for a full understanding of the present invention.

The present invention provides several important advantages over the prior art. It does not require measurements of the pressure differential across the diaphragm, so the patient does not have to swallow pressure transducers, or suffer other invasive procedures. This makes the method according to the invention especially valuable for patients with severe breathing problems. It can even be used on patients requiring assisted breathing from respirations, as explained above. The invention is, however, equally applicable to healthy patients.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. A method for non-invasive evaluation of diaphragmatic function, comprising the steps of:
   (a) real time ultrasonic measuring of the thickness of a diaphragm in a patient; and
   (b) displaying said diaphragm thickness as a function of time.

2. A method for non-invasive evaluation of diaphragmatic function as claimed in claim 1, comprising the further steps of:
   (c) performing a breathing test wherein the patient breathes at a steady rhythm while attempting to maintain a constant pattern for said displayed diaphragm thickness as a function of time; and
   (d) measuring the time period from the start of the breathing test until the patient is no longer able to maintain said constant pattern.

3. A method for non-invasive evaluation of diaphragmatic function as claimed in claim 2, wherein step (c) further comprises the substeps of:
   adding a pressure regulator designed to hold a constant pressure differential;
   having the patient breathe through said pressure regulator.

4. A method for non-invasive evaluation of diaphragmatic function as claimed in claim 3, comprising the further step of:
   (e) adjusting said pressure differential for successive breathing tests.

5. A method for non-invasive evaluation of diaphragmatic function as claimed in claim 3, wherein said pressure differential is negative, so the pressure regulator aids the patient in breathing.

6. Apparatus for non-invasive evaluation of diaphragmatic function, comprising:
   (a) an ultrasonic transducer arrangeable on the lower rib cage of a patient between ribs to transmit an ultrasonic pulse through the lateral part of the patient's diaphragm and to receive pulse echoes from the inside of the rib cage;
   (b) means for receiving and amplifying ultrasonic signals received by said transducer;
   (c) means for selecting a pair of signals reflected from the parietal pleura side and the peritoneum side of the diaphragm;
   (d) means for determining the time differential between said pair of signals;
   (e) means for repeating the pulse transmission at constant time intervals; and
   (f) means for displaying said time differentials between said pair of signals from subsequent pulse transmissions versus time.

* * * * *